United States Patent [19]

Carter et al.

[11] 4,251,672

[45] Feb. 17, 1981

[54] PROCESS FOR HYDROGENATING ORGANIC COMPOUNDS WITH COPRECIPITATED COPPER-NICKEL-SILICA CATALYSTS

[75] Inventors: James L. Carter; Allan E. Barnett, both of Westfield, N.J.

[73] Assignee: Exxon Research & Engineering Co., Florham Park, N.J.

[21] Appl. No.: 936,776

[22] Filed: Aug. 25, 1978

Related U.S. Application Data

[60] Division of Ser. No. 819,346, Jul. 27, 1977, abandoned, which is a continuation-in-part of Ser. No. 729,721, Oct. 5, 1976, abandoned, which is a continuation of Ser. No. 577,328, May 14, 1975, abandoned.

[51] Int. Cl.$^3$ .......................... C07C 5/10; C07C 5/02
[52] U.S. Cl. .............................. 568/814; 568/881; 568/852; 585/250; 585/276; 585/258; 585/259; 585/261; 585/269; 585/270; 260/393; 260/563
[58] Field of Search ............... 252/452, 459; 208/143; 585/270, 277; 568/881, 814

[56] References Cited

U.S. PATENT DOCUMENTS

| 1,823,865 | 9/1931 | Swallen | 252/452 |
|---|---|---|---|
| 2,034,077 | 3/1936 | Arnold et al. | 252/454 |
| 2,750,261 | 6/1956 | Ipatieff et al. | 252/459 |
| 3,371,050 | 2/1968 | Taylor et al. | 252/459 |
| 3,859,370 | 1/1975 | Carter et al. | 585/277 |
| 3,868,332 | 2/1975 | Carter et al. | 252/459 |
| 4,075,251 | 2/1978 | Mertzweiller et al. | 568/881 |
| 4,088,603 | 5/1978 | Carter et al. | 252/459 |

OTHER PUBLICATIONS

H. Charcosset et al., J. Catalysis, 22, 204–212, 1971.
J. H. Sinfelt et al., J. Catalysis, 24, 283–296, 1972.
D. J. C. Yates et al., J. Amer. Chem. Soc. 86, 2996–3001, 1964.
J. H. Sinfelt, Science, 195, 641–646, 1977.
A. Roman et al., J. Catalysis 30, 333–342, 1973.

*Primary Examiner*—Veronica O'Keefe
*Attorney, Agent, or Firm*—Albert P. Halluin

[57] ABSTRACT

A copper promoted massive nickel catalyst is disclosed which is capable of having a reduced nickel surface area ranging from about 55 to about 100 m$^2$/g as determined by hydrogen chemisorption, after reduction at 400° C., and a B.E.T. total surface area ranging from about 150 to about 300 m$^2$/g, wherein the amount of copper in the catalyst ranges from about 2 wt. % to about 10 wt. % and the amount of nickel ranges from about 25 wt. % to about 50 wt. %, said wt. % of copper and nickel metal are based on the total weight of the catalyst. The copper promoted massive catalysts are prepared by the steps comprising comingling a solution containing copper and nickel cations with another solution containing silicate anions and coprecipitating the copper, nickel and silicate ions in an aqueous solution onto solid carrier particles. The catalysts are useful in hydrogenation processes.

15 Claims, No Drawings

PROCESS FOR HYDROGENATING ORGANIC COMPOUNDS WITH COPRECIPITATED COPPER-NICKEL-SILICA CATALYSTS

CROSS REFERENCE TO RELATED APPLICATIONS

This is a division of application Ser. No. 819,346, filed July 27, 1977, now abandoned; and which is a continuation-in-part of Ser. No. 729,721, filed Oct. 5, 1976, now abandoned; which is a continuation of Ser. No. 577,328, filed May 14, 1975, now abandoned.

BACKGROUND OF THE INVENTION

A. Field of the Invention

This invention relates to copper promoted highly active nickel-silica catalysts having stabilized high nickel surface areas which contain very little quantities of alkaline metals, their preparation and use in the hydrogenation of organic compounds. In one aspect, this invention relates to the addition of copper in the preparation of a massive nickel hydrogenation catalyst thereby facilitating the low temperature reduction of the catalyst. In another aspect, this invention relates to the preparation of novel activated nickel copper hydrogenation catalysts. In yet another aspect, this invention relates to charging the copper nickel silica catalyst into the hydrogenation plant without undergoing the customary prereduction and stabilization steps that are required for the commercial hydrogenation catalysts now being employed.

B. Description of the Prior Art

The so-called activation of supported nickel catalysts, i.e., the reduction of nickel oxide before the catalyst is utilized, is usually conducted at temperatures which are very high in comparison to those at which the reduction of bulk nickel oxide can be completed. It is a well-known fact that supported nickel oxide is more difficult to reduce than when unsupported and that high reduction temperatures promote sintering of nickel. It is thought that, in many instances, a better activity and/or a better poison capacity could be obtained, if lower reduction temperatures could be used.

In conformity with the experience of people concerned with catalyst manufacture, recent publications suggest that various promoters of nickel catalyst are effective not because of some modification of the catalytic properties, but as a consequence of a better activation.

A. Roman and B. Delmon in an article from the *Journal of Catalysis*, 30, pp. 333-342 (1973) entitled "Promoter and Carrier Effects in Reduction of $NiO/SiO_2$" have described the hydrogen reduction of nickel oxide deposited on silica by employing copper deposited onto the surface of the catalyst.

In another paper published in the *Journal of Catalysis*, 22, pp. 204-212 (1971) entitled "Increase of Reducibility of NiO by $H_2$, Due to Pretreatment with Salt Solutions" by H. Charcosset, R. Frety, A. Soldat and Y. Trambouze, also describes the use of copper in the treatment of pure nickel oxide to make the reduction easier. In this paper, they also impregnated the nickel oxide catalyst with various salt solutions followed by drying and extraction with water. They then compared the reduction of these catalysts in hydrogen to see which metals had the most effect. They indicated most pronounced effects occur with copper, platinum, palladium, ruthenium, rhodium, osmium, iridium which they stated are related to a cationic exchange with surface nickel during impregnation.

More recently, in a paper published in the *Journal of Catalysis*, 24, pp. 283-296 (1972) entitled "Catalytic Hydrogenolysis and Dehydrogenation Over Copper-Nickel Alloys" by J. H. Sinfelt, J. L. Carter and D. J. C. Yates, there is described the surprisingly large effects on suppression of hydrocracking from the incorporation of small amounts of copper into nickel in a copper/nickel alloy.

The patent literature also includes descriptions of nickel catalysts which contain copper. One example of such a description is disclosed in U.S. Pat. No. 2,750,261 to Ipatieff et al. In this patent there is disclosed a process for preparing catalyst useful in the production of hydrogen comprising the steps of co-precipitating a mixture of nickel and copper ions onto a carrier such as diatomaceous earth. A comparison of the catalyst prepared in accordance with Example II of this patent with the instant catalyst is disclosed in Examples 6 and 7 of the instant application.

The copper promotion of the subject invention relates to the massive nickel catalyst described in U.S. Pat. Nos. 3,697,445 and 3,859,370. These patents describe catalysts having high nickel surface area and the relationship between the high nickel surface area and their activity. The nickel surface area is measured by hydrogen chemisorption, after reduction at 400° C., in the manner described by Yates, Taylor and Sinfelt, in *J. Am. Chem. Soc.*, 86, 2996 (1964).

In U.S. Pat. No. 3,859,370 there is described a process for carefully controlling critical conditions to form these high nickel surface area catalysts wherein nickel catalysts precipitated in the presence of porous solid particles can be made which have a nickel surface area greater than about 70 $m^2/g$, preferably 75 to 100 $m^2/g$ and catalytic activity for hydrogenation several times greater than the previously known nickel catalysts.

The massive nickel catalysts described in the aforesaid U.S. Pat. Nos. 3,697,445 and 3,859,370 have proven to be active hydrogenation catalysts in laboratory and pilot plant runs when they are activated by reduction at 400° C. However, there is a need to have such a catalyst that can be activated at the lower temperatures than are normally obtainable in the commercial hydrogenation plant which is approximately 200° C.

DISCOVERY OF THE PRESENT INVENTION

It has been discovered that the presence of copper ions during the co-precipitation of the nickel and silica ions provides a catalyst which can be activated at lower temperatures than are normally required for nickel-containing hydrogenation catalysts. Specifically, it has been found that by the incorporation of copper in a massive nickel catalyst during the co-precipitation provides a highly active hydrogenation catalyst which can be activated at temperatures of approximately 200° C.

SUMMARY OF THE INVENTION

In one embodiment of the present invention there is provided a copper promoted massive nickel catalyst which is capable of having a reduced nickel surface area ranging from about 55 to about 100 $m^2/g$ as determined by hydrogen chemisorption after reduction, at 400° C., and a B.E.T. total surface area ranging from about 150 to about 300 $m^2/g$. The B.E.T. total surface area preferably ranges from about 225 to about 300 $m^2/g$. The amount of copper in the catalyst preferably ranges from about 2 wt. % to about 10 wt. % and the amount of nickel preferably ranges from about 25 wt. % to about 50 wt. %, said wt. % of copper and nickel are based on the total weight of the catalyst.

In another embodiment of the present invention the copper promoted massive nickel catalysts are prepared by the steps comprising comingling a solution containing copper and nickel cations with another solution containing silicate anions and thereafter coprecipitating the copper, nickel and silicate ions in an aqueous solution onto solid carrier particles.

In still another embodiment of the present invention there is provided a process for hydrogenating organic compounds by contacting a hydrogenatable organic compound with hydrogen in the presence of a reduced copper promoted massive nickel-silica catalyst capable of having a reduced metal surface area ranging from about 55 to about 100 m$^2$/g as determined by hydrogen chemisorption, after reduction at 400° C., and a B.E.T. total surface area ranging from about 150 to about 300 m$^2$/g, and preferably from about 225 to about 300 m$^2$/g.

DESCRIPTION OF THE PREFERRED EMBODIMENTS

In the preferred embodiment of this invention, the catalyst contains from 2% to 10% by weight copper, has a reduced nickel surface area ranging from about 55 to about 100 m$^2$/g, after reduction at 400° C. as determined by hydrogen chemisorption, a B.E.T. total surface area ranging from about 150 to about 300 m$^2$/g and sodium content of about 0.1 wt. % or lower based on the total weight of active catalyst.

The nickel surface area as referred to herein is determined by hydrogen chemisorption, after reduction at 400° C. unless otherwise specified, in the manner described by Yates, Taylor and Sinfelt in *J. Am. Chem. Soc.*, 86, 2996 (1964), the disclosure of which is incorporated herein by reference.

Unlike the prior art publications and patents that show the addition of copper to the surface of the nickel oxide, the copper must be added to these massive nickel systems during the precipitation stage through the use of separate solutions which are preferably aqueous in nature. In a first solution, there is dissolved a source of silicate anion and in a second solution, a source of nickel cation and copper cation. Slurried within the solution containing the silicate anion is a porous support, preferably a porous silica support such as kieselguhr. The two solutions are comingled by addition of the nickel-copper containing solution to the silicate solution over a period of approximately 5 to 40 minutes. By comingling the two previously prepared solutions, the amount of dissolved nickel in the reaction mixture is kept exceedingly low and in general well below 0.60 moles/liter of aqueous mixture. This dilution of the dissolved nickel ions is essential in obtaining high nickel surface area catalysts. Also, the addition should be made at a substantially constant rate accompanied by vigorous mixing to increase uniformity in the catalyst formation. The mixture is then heated to its boiling point and a precipitating agent is added. A commonly used precipitating agent is ammonium bicarbonate.

During the preparation water is added to maintain a nearly constant volume so that water lost by evaporation is continually replaced. The aqueous mixture is kept at its boiling point for a period of 1 to 5 hours; it is then filtered and the resulting product is washed repeatedly with boiling water. Next the catalyst is dried and calcined in an oxygen source. The finished catalyst can then be charged directly (or subsequent to shaping such as in the form of pellets) into the reaction vessel, without activation, and activated in the reaction vessel with a gaseous reductant, usually flowing hydrogen.

As stated previously, the copper-nickel containing solution and the silicate-containing solution are comingled under conditions of dilution such that the amount of dissolved nickel ions in the resultant aqueous mixture is maintained exceedingly low thereby providing for a high nickel surface area catalyst. Additionally, however, it is essential in preparing the catalyst of this invention, that the precipitation of the catalyst be made from dilute solutions, i.e., the nickel-containing solution must have a nickel concentration no greater than 1.0 moles/liter and the other solution a silicate ion concentration no greater than 0.35 moles/liter. The copper concentration is determined by the desired amount of copper in the catalyst. The most preferred solution used in preparing the catalyst has no more than 0.75 moles/liter of nickel and 0.26 moles/liter of silicate ion. This is contrasted with a more concentrated precipitation in which the solution contains up to twice as much solute.

About 30 to 90 wt. % of the total silica content of the activated catalyst derives from precipitated silicate ions. Preferably, however, 50 to 70 wt. % of the total silica content is derived from silicate ions.

The remaining steps in preparing and activating the catalyst are identical to those described above.

In more detail, the instant invention pertains to the production of an improved catalyst for hydrogenation. The catalyst may be used to hydrogenate aromatics as typified by the hydrogenation of benzene to cyclohexane, the hydrogenation of aldehydes, both saturated and unsaturated to the alcohols as in the well-known oxo process, the hydrogenation of the double bonds in edible fats and oils as well as other olefins both straight and branched chain, the hydrogenation of aromatics in white oil base stocks to produce high grade white oils and the hydrogenation of nitro compounds to amines. Indeed, olefins as used herein signify unsaturated compounds having at least one multiple bond and contemplate polyunsaturated compounds as well.

To form the catalyst, nickel and copper, as well as the silicate ions must be coprecipitated onto a porous solid particulate support, preferably a porous silica particulate support. Initially, two distinct solutions are prepared; in one of these solutions is a silicate ion source such as alkali silicates, i.e., sodium and potassium silicates, sodium meta silicate, etc., or salicic acid and porous solid particles.

A second solution, containing a source of nickel cation and copper cation is also prepared; the source of nickel cation may be any of the following: nickel nitrate, nickel chloride and nickel bromide. The source of copper cation may be also copper nitrate, copper chloride and copper bromide.

Other sources of nickel cation and silicate anion may be utilized and will be obvious to one skilled in the art.

Porous solid particles, preferably silica particles, will be slurried in the silicate anion solution. In particular, kieselguhr, infusorial earth, diatomaceous earth, siliceous earth, silica or alumina would be the source of the porous particles. The concentration of the porous solid particles can be expressed as percent of the total silica in the catalyst and should be from 10 to 70%, preferably from 30 to 50% by weight.

The two solutions, one solution containing copper and nickel cations, the other containing the silicate anion are comingled at a slow rate to effect maximum mixing. Typically, the nickel and copper nitrate solution would be added to a sodium meta silicate solution uniformly over approximately a 5 to 40 minute period, preferably 10 to 30 minute period. The mixture is then heated to the boiling point and coprecipitation of copper nickel and silicate ions must be completed. This may be effected by various methods known in the art, but it is most preferred that the coprecipitation of copper nickel and silicate ions in aqueous solution containing the solid carrier particles be completed by addition of a water soluble alkaline precipitating compound such as ammonium bicarbonate. The alkaline ammonium precipitants are most suitable for minimizing the amount of alkali metal residue which has to be removed by washing to avoid poisoning action on the finished catalyst. In some instances, the potassium precipitants may be used where the potassium acts as a promoter rather than as a poison. Sodium carbonate is still another example of a suitable water soluble alkaline precipitating compound.

The salts of the metal are preferably the water-soluble compounds, e.g. nitrates, chlorides, formates or oxalates. The preferred catalytic metal is nickel but other non-noble Group VIII catalytic metals may be used; these metals include cobalt and iron.

Following the precipitation, the mixture is maintained at the boiling point for about 1 to 5 hours; than it is filtered and washed 4 times with boiling water. Precipitated catalyst is then dried by heating for about 1 to 5 hours at a temperature of 90° to 200° C. It is then calcined by heating in the presence of an oxygen-containing gas or air to a temperature in the range of 300° to 450° C. for a period of 2 to 8 hours, preferably 3 to 5 hours.

After the calcining is completed, the catalyst must be reduced in order to activate it. Reduction is carried out in the presence of a reducing gas which is preferably hydrogen. Hydrogen is passed over the catalyst at ambient temperature at a rate of 5 l./Hr./gm. to 30 l./Hr./gm. and then the temperature is raised to a range from 75° C. to 400° C., preferably 80° C. to 250° C.

The reduction is preferably carried out after the catalyst has been loaded into the reaction vessel, where the hydrogenation will be carried out, which may be either batch or continuous. The nature of the reactor will be obvious to one skilled in the art.

The resulting catalyst preferably is capable of having a nickel surface area ranging from about 55 to 100 $m^2/g$ as determined by hydrogen chemisorption, after reduction at 400° C., and a B.E.T. total surface area ranging from about 150 to about 300 $m^2/g$. Also, the catalyst preferably contains about 0.1 wt. % or less of sodium and preferably from 25 wt. % to about 50 wt. % of nickel.

One particularly useful hydrogenation is the conversion of benzene to cyclohexane.

Another useful hydrogenation is the conversion of aromatics in white spirits to yield high quality solvents. The upgrading of white spirits by the process of this invention is an improvement in the treatment of such materials.

Another useful improved hydrogenation is the conversion of olefins in paraffin solvents such as denonenizer bottoms and deoctenizer overheads.

The conditions for the hydrogenation reactions which have been discussed vary widely and are well known to those skilled in the art; broadly the following conditions may be utilized: temperatures ranging from about 75°–300° C.; pressure 1 atm.–12,000 psig; a space velocity feed rate ranging from about 0.2–100 V/Hr/V; and a $H_2$ rate ranging from 500–10,000 SCF/B.

The oxo process is the addition of carbon monoxide and hydrogen to alkenes in order to produce alcohols, aldehydes and other oxygenated organic compounds. Typical alkenes which may be utilized in the process are those having 2 to 20 carbon atoms; conditions for oxo would be temperatures of 70° to 175° C.; hydrogen to hydrocarbon mol ratio of 0.5 to 10.0 pressure of 100 to 1000 psig.

The product of such a carbonylation process generally consists of aldehydes, acetals, unsaturated oxygenated materials and the like which require hydrofinishing in a second or further hydrogenation stage. It is to the treatment of the aldehyde product, in particular, that the present invention applies.

Hydrogenation conditions in this further reaction stage follow those generally employed in the first stage.

The following examples serve to more fully describe the manner of making and using the above-described invention, as well as to set forth the best modes contemplated for carrying out various aspects of the invention. It is understood that these examples in no way serve to limit the true scope of this invention, but rather, are presented for illustrative purposes.

EXAMPLE 1

Catalyst A was prepared as follows: 8.75 gm. of Cu(NO$_3$)$_2$.3H$_2$O and 112 gm. of Ni(NC$_3$)$_2$.6H$_2$O were dissolved in 500 ml of distilled water, then 38 gm. of Na$_2$SiO$_3$.9H$_2$O was dissolved in another 500 ml of water and 5 gm. of acid washed kieselguhr was slurried in this second solution. The second solution with the kieselguhr slurried therein was stirred vigorously while the first solution containing the copper and nickel salts was added at a uniform rate over a 20 minute period. This mixture was then heated to the boiling point and 80 gm. of NH$_4$HCO$_3$ was added at a uniform rate over a 20 minute period. The mixture was kept at the boiling point for 3 hours while stirring continued. It was then filtered and washed 5 times with boiling water, each wash consisting of 500 ml of water. The filter-cake was then dried at 120° C. and calcined in air for 4 hours at 400° C. The reduced nickel surface area of Catalyst A was determined by hydrogen chemisorption, after reduction at 400° C., to be 62.0 $m^2/g$.

Catalyst B was prepared in the same manner as Catalyst A with the exception that there was no copper added. Catalyst B had a reduced nickel surface area of 65 $m^2/g$ as determined by hydrogen chemisorption after reduction at 400° C. and a B.E.T. total surface area of 292 $m^2/g$.

Table I demonstrates the data from thermogravametric analysis experiments which are presented for two massive nickel catalysts; one with 5% copper (Catalyst A) added during the precipitation step and the other (Catalyst B) without any copper added. The Table shows that the copper-containing catalyst starts to reduce significantly at about 200° C. lower than the catalyst without copper. It also shows that Catalyst A is substantially reduced at temperatures that can be reached in commercial hydrogenation plants whereas Catalyst B does not start to reduce significantly below about 350° C.

EXAMPLE 2

The data in Table II compares two catalysts for the hydrogenation of benzene. They are Catalyst A and a catalyst made by the same procedure as Catalyst A (Catalyst E) but there was no copper used in the preparation. The catalysts were pre-reduced and stabilized then re-reduced in the reactor at 204° C. This temperature is not adequate to activate the catalyst that does not contain copper and it can be seen that the conversion of benzene to cyclohexane is much greater over the copper containing catalyst.

TABLE I

| Temp. | Extent of Reduction Based on reductive and nonreductive thermogravemetric analysis | |
|---|---|---|
| | CATALYST A | CATALYST B |
| 100° C. | 9% | 14% |
| 150° C. | 2% | 17% |
| 200° C. | 2% | 18% |
| 250° C. | 0% | 18% |
| 300° C. | 2% | 19% |
| 350° C. | 00% | 21% |
| 400° C. | 00% | 23% |
| 450° C. | 00% | 27% |

TABLE II

| | Catalyst A 5% copper | Catalyst E No copper |
|---|---|---|
| Conversion of benzene to cyclohexane after 1 hour on stream | 30.5% | 15% |
| | Run Conditions: Temp. 100° C. Press. 1 atm. S.V. 25 W/Hr/W H$_2$/C$_6$H$_6$ mol ratio | |

EXAMPLE 3

Catalyst C, which was prepared in the same manner as (Catalyst A) of Example 1, was tested and compared with Catalyst B in a manner designed to simulate conditions used in solvent hydrogenation. Catalyst C had a reduced nickel surface area of 65.4 m$^2$/g as determined by hydrogen chemisorption after reduction at 400° C. and a B.E.T. total surface area of 275 m$^2$/g. The feed was 15% benzene in cyclohexane and the pressure was 70 psig. The data in Table III show that Catalyst C can be activated under conditions used in the plant and has high activity whereas the catalyst without copper (Catalyst B) shows almost no activity.

TABLE III

| | Temp. °C. | S.V. W/Hr/W | % C$_6$H$_6$ | % Conversion of the C$_6$H$_6$ |
|---|---|---|---|---|
| Catalyst C 5% Cu | 200 | 18.8 | 0 | 100 |
| Catalyst B No Cu | 202 | 18.8 | 14.9 | 0.7 |
| Run Conditions: Press. 70 psig, H$_2$ to hydrocarbon 0.5 mol. ratio Feed, 15% benzene in cyclohexane | | | | |

EXAMPLE 4

A further illustration of the low temperature activation of the catalyst of the present invention is given in Table IV where the active nickel surface area for two catalysts, with and without copper, which were obtained after reduction at 200° C., are shown. Catalyst D was prepared in the same manner as Catalyst B of Example 1. (Catalyst C had a reduced nickel surface area of 65.4 m$^2$/g and Catalyst D has a reduced nickel surface area of 64.3 m$^2$/g, both as determined by hydrogen chemisorption after reduction at 400° C.)

TABLE IV

| | Catalyst C 5% Cu | Catalyst D No copper |
|---|---|---|
| Reduced nickel surface area, m$^2$/gm. catalyst after reduction at 200° C. | 34.1 | 3.9 |

The results of this data indicate that the new copper nickel-silica catalyst disclosed in this example can be charged into the hydrogenation plant without undergoing the customary prereduction and stabilization steps that are required for the commercial hydrogenation catalysts now being used. It is clearly shown that the catalyst containing the copper is easily reduced and develops a substantial reduced (active) nickel surface area whereas the catalyst without copper does not reduce nor develop an active nickel surface area to any significant extent.

EXAMPLE 5

This experiment was run to show the importance of adding the copper during the precipitation of the catalyst. In Catalyst A (as prepared in Example 1), the copper was coprecipitated with the nickel, as taught in the instant patent application. Catalyst F was prepared by impregnating copper on the dried but uncalcined powder used to make Catalyst B. Specifically, Catalyst F was prepared by impregnating 6.85 grams of the powder with 4.8 ml of an aqueous solution of Cu(NO$_3$)$_2$.3-H$_2$O of proper concentration to give 5% copper on the reduced catalyst. The catalyst was then dried at 230° F. and calcined 4 hours at 750° F. The results are shown in Table V.

TABLE V

| | Catalyst A % Extent of Reduction Based on Total Loss | |
|---|---|---|
| Temp. °C. | in H$_2$ at 700° C. | Catalyst F |
| 0 | 0 | |
| 100 | 11 | 11 |
| 150 | 24 | 16 |
| 200 | 33 | 20 |
| 250 | 42 | 23 |
| 300 | 52 | 25 |
| 350 | 63 | 29 |
| 400 | 75 | 36 |
| 450 | 84 | 50 |

These results demonstrate the criticality in coprecipitating the Cu and Ni ions with the silicate anions as opposed to adding them to the surface of the NiO as taught in the prior art.

EXAMPLE 6

This experiment was performed to compare the catalyst preparation of Example II of U.S. Pat. No. 2,750,261 to Ipatieff et al with the catalyst of the present invention. Catalyst G, the catalyst prepared in accordance with Example II of U.S. Pat. No. 2,750,261 was prepared by dissolving 6.1 g. of CuSO$_4$.5H$_2$O and 60.7 g. NiSO$_4$.6H$_2$O in 1200 ml water. To this mixture, under agitation, there was added 5.8 g. of kieselguhr and the mixture was gradually heated to 70° C. To the heated mixture there was added 46.2 g. $Na_2CO_3$ dissolved in 200 ml water while rapidly mixing the mixture and maintaining the temperature at about 70° C. The mixture was allowed to stand for 3 days whereupon a precipitate was washed by decantation and on a suction filter with distilled water. The washing was continued until the filtrate was free of sulfate ions (as determined by the $BaCl_2$ test). The filter cake was dried at 110° C. and thereafter calcined for 3 hours at 662° F. (350° C.) in a stream of nitrogen until the evolution of carbon dioxide practically ceased. The catalyst preparation was split into aliquots, one of which was reduced overnight (16 hours) in hydrogen at 538° C. and another being reduced overnight (16 hours) at 400° C. The nickel surface area of the two catalyst samples was determined by the procedure described by Yates, Taylor and Sinfelt in *J. Am. Chem. Soc.*, 86, 2996 (1964). The catalyst sample reduced at 538° C. prepared in accordance with Example II of U.S. Pat. No. 2,750,261 had a nickel surface area of 30 $m^2/g$ (Catalyst G), whereas the catalyst sample prepared in accordance with Example II of U.S. Pat. No. 2,750,261, but reduced at 400° C. has a nickel surface area of 49 $m^2/g$ (Catalyst G). The B.E.T. total surface area of Catalyst G following calcination but prior to reduction was 126 $m^2/g$.

EXAMPLE 7

The following experiment illustrates the superiority of the catalyst of the present invention (Catalyst H) with the catalyst sample prepared in accordance with Example II of U.S. Pat. No. 2,750,261, but reduced at 400° C. (Catalyst G). The catalyst of the present invention (Catalyst H) and Catalyst G were used to hydrogenate benzene in the manner described below.

Pressure: 1 atmosphere
Temperature: Catalyst G 77° C.; Catalyst H 76° C.
Feed: 90% n-hexane; 10% benzene
Feed rate: 20 cc/hr
$H_2$ rate: 20.4 1/hr
Catalyst Charge: 0.25 gm; Catalyst reduced 16 hr. at 400° C.

TABLE VI

| Aromatic Hydrogenation | | | |
|---|---|---|---|
| Catalyst G | | Catalyst H[1] | |
| Time | Benzene Conversion | Time | Benzene Conversion |
| 25 min. | 19.6% | 15 min. | 40.6% |
| 80 min. | 17.8% | 30 min. | 40.6% |
| 155 min. | 17.1% | 45 min. | 43.4% |
| 180 min. | 17.0% | 60 min. | 42.6% |
| | | 105 min. | 40.0% |
| | | 255 min. | 38.5% |

[1]Catalyst prepared in accordance with the procedure described in Example 1. The catalyst had a nickel surface area of 61.3 $m^2/g$ as determined by hydrogen chemisorption when reduced at 400° C. and a B.E.T. total surface area of 259 $m^2/g$.

The data in Example 7 show that the catalyst of the present invention has a higher selective activity for hydrogenating benzene than does the Catalyst G, the catalyst prepared in accordance with Example II of U.S. Pat. No. 2,750,261, even though the latter catalyst, when reduced at 400° C. has a relatively high nickel surface area. Also, the data in Example 6 indicates that the catalyst prepared in accordance with Example II of U.S. Pat. No. 2,750,261 has a slightly lower nickel surface area and a lower B.E.T. total surface area than the catalysts of the present invention.

EXAMPLE 8

This experiment illustrates that the catalyst of the present invention can be prepared in large quantities while retaining the desired properties of nickel surface area, B.E.T. total surface area and selective hydrogenation properties.

A first solution was prepared to contain 2,466 pounds of $Ni(NO_3)_2.6H_2O$ and 166 pounds of $Cu(NO_3)_2.3H_2O$ in 1,300 gal. of water. 625 pounds of $Na_2SiO_3.5H_2O$ was dissolved in another vessel containing 1,300 gal. of water. 112 pounds of kieselguhr was added to this second aqueous solution. The second solution with the kieselguhr slurried therein was stirred vigorously while the first solution containing the copper and nickel salts was added thereto at a uniform rate over a 1 hour time period. The total water content in the agitated slurry after combination was 2,600 gallons. The total mixture was then heated to the boiling point and 1,766 pounds of $NH_4HCO_3$ was added at a uniform rate over a 1 hour time period. The mixture was kept at the boiling point for about 5 hours while stirring continued. The catalyst was then washed continuously and tray dried at 300° F. The catalyst preparation was then batch calcined in an air recirculating oven at a final temperature of 750° F. The catalyst (Catalyst I) was analyzed to have the following characteristics and properties (after pilling).

TABLE VII

| Catalyst I | |
|---|---|
| Nickel | 45 wt. % |
| Copper | 4.5 wt. % |
| Sodium | 0.05 wt. % |
| Apparent bulk density | 0.85 gm/ml |
| B.E.T. total surface area | 250 $m^2/g$ |
| Active nickel surface area by $H_2$ chemisorption | 52 $m^2/g$ |

This catalyst (in pill form) was subsequently used to hydrogenate white spirits containing aromatics in a continuous reactor under the following reaction conditions.

Pressure: 600 psi
Temperature: 320° F.
Space Velocity: 30 V/Hr/V
$H_2$: 1,000 SCF/B The results of this hydrogenation experiment are shown in the following table.

TABLE VIII

| Aromatic Hydrogenation | | |
|---|---|---|
| Time on Feed | Aromatic Conversion, %* | |
| Hours | ¼" pills | 3/16" pills |
| 30 | 60 | 40 |
| 50 | 48 | 34 |
| 55 | 47 | 33 |
| 76 | 42 | 28 |
| 84 | 44 | 28 |
| 100 | 38 | 28 |
| 108 | 36 | 24 |
| 122 | 37 | 28 |

*The catalyst was activated by raising the temperature to 475° F. during the first 12 hours of the test then subsequently lowered to the test condition of 320° F.

EXAMPLE 9

The procedure in Example 8 was repeated to prepare a large batch of the catalyst (Catalyst J) except that the precipitated and washed catalyst was spray dried and calcined in a rotary kiln at a final temperature up to 750°

F. rather than tray dried and batch calcined. Another batch of catalyst was prepared (Catalyst K) by the procedure of Example 8 except Na₂CO₃ was used in place of NH₄HCO₃ as the precipitating agent. Furthermore, the catalyst was spray dried prior to washing. Both catalysts were analyzed to have the following characteristics and properties (after pilling).

TABLE IX

|  | Catalyst J | Catalyst K |
|---|---|---|
| Nickel, % wt. | 44 | 45 |
| Copper, % wt. | 4.5 | 4.6 |
| Sodium, % wt. | 0.09 | 0.03 |
| Apparent bulk Density g/ml | 0.72 | 0.66 |
| lb/ft³ | 45 | 41 |
| B.E.T. surface area, m²/g | 257 | 260 |
| Active Nickel Surface Area by H₂ chemisorption, m²/g | 58.7 | 56.3 |

These catalysts (in pill form) were subsequently used to hydrogenate white spirits containing aromatics in a continuous reactor under the following reaction conditions.

Pressure: 500 psi
Temperature: 320° F.
Space Velocity: 30 V/Hr/V
H₂: 1,000 SCF/B The results of this test are shown in the following table:

TABLE X

| | Aromatic Hydrogenation | |
|---|---|---|
| | Aromatic Conversion, %* | |
| Time on Feed, Hours | Catalyst J | Catalyst K |
| 2 | 80 | 90 |
| 2 | 78 | 88 |
| 3 | 75 | — |
| 4 | 73 | — |
| 5 | — | 82 |
| 6 | 69 | — |
| 7 | 68 | — |
| 8 | 65 | — |
| 9 | 63 | — |
| 10 | — | 72 |
| 11 | 60 | — |
| 12 | — | 63 |
| 14 | 57 | — |
| 40 | — | 50 |

*The catalyst was activated by raising the temperature to 475° F. during the first 12 hours of the test then subsequently lowered to the test condition of 320° F.

As can be seen from the data in Tables VIII and X, the catalyst of the present invention not only possess a high selective activity for converting aromatics, but they are able to retain their activity for prolonged use under continuous reaction conditions.

GENERAL

The incorporation of a small amount of copper as a coprecipitant with the nickel in the catalyst of the present invention provides two beneficial effects, i.e., lower temperatures of activation and suppression of hydrocracking.

Conventional nickel catalysts must be activated in situ at up to 425° C. (800° F.) to obtain optimum activity. Alternately, prereduced and stabilized forms of conventional catalysts have been made available which enable activation of the catalyst when the higher temperatures are not attainable in situ in plant equipment. Prereduction and stabilization add process steps and attendant costs in the manufacture of conventional catalysts.

The copper present in the catalysts of the present invention promotes in situ activation of the catalyst at temperatures below 230° C. (450° F.). This ability to promote activation avoids the installation of expensive furnaces for catalyst activation. Or, in existing equipment with lower temperatures, it eliminates the need for a prereduced and stabilized catalyst. Elimination of the prereduction and stabilization steps would be expected to provide a cost advantage of the catalysts of the present invention, longer range.

In addition to lowering the temperature for activating the catalyst of the present invention, the small amount of copper present significantly inhibits the amount of hydrocracking side reactions which take place during hydrogenation. This result is in general agreement with reported literature findings on the effect of copper in copper/nickel alloys on the suppression of hydrocracking. (Cf. J. H. Sinfelt, J. L. Carter, D. C. Yates, *Journal of Catalysis*, 24 (2), 283–296 (1972) and J. H. Sinfelt, *Science*, 195, 641–646 (1977)). As shown from the following table, a temperature "safety cushion" of about 100° F. prior to the onset of runaway hydrocracking was observed with the catalyst of the present invention when compared to a commercially available nickel catalyst (Catalyst L).

TABLE XI

| Bulk Bed Temperatures at the Onset of Runaway Hydrocracking[1] | | |
|---|---|---|
| | Bed Inlet | Maximum in Bed |
| Catalyst L | 528° F. | 587° F. |
| Catalyst A[2] | 622° F. | 679° F. |

[1]Mineral spirits feed, 600 psig, 2000 SCF/bbl H₂
[2]Catalyst was prototype prepared by the procedure described in Example 1 for Catalyst A.

Thus, from the standpoint of operational safety in large scale operations, the catalyst of the present invention offers an additional margin of safety for averting temperature runaways due to hydrocracking where the potential exists. In addition, there is evidence that the catalyst of the present invention inhibits hydrocracking side reactions during hydrogenation which in some cases can increase selectivity, decrease light ends and gas make, decrease hydrogen comsumption, and create significant yield benefits.

For example, tests on Catalyst I (Example 8) have shown a yield benefit of 3–6% when compared with continuous runs with conventional nickel catalysts in the hydrogenation of solvent feeds.

In addition to the high B.E.T. surface area of the catalyst of the present invention as previously disclosed, it is to be noted that the catalyst has a relatively low apparent bulk density (ABD). Replacement of a conventional massive nickel catalyst in an existing unit by the lower density catalyst of the present invention can result in superior hydrogenation performance despite the significantly lower weight of the catalyst of the present invention charged to a reaction vessel. The following table describes the preferred characteristics of the catalysts of the present invention.

TABLE XII

| Nickel Content, % wt. | 43–46 |
|---|---|
| Copper, % wt. | 4.4–5.0 |
| Sodium content | <0.1 |
| B.E.T. Surface Area, m²/g | 225–300 |
| Apparent bulk density | |

TABLE XII-continued

| | |
|---|---|
| g/ml | 0.70–0.90 |
| lbs/ft³ | 44–55 |
| Crush, lbs | |
| ¼" × ¼" cylinders | 6–10 |
| 3/16" × 3/16" cylinders | 12–16 |

The catalyst of the present invention is applicable to a plurality of end use hydrogenations, i.e. (1) benzene to cyclohexane (2) 2-ethylhexenal to 2-ethylhexanol, (3) olefins to paraffins and (4) aromatics to naphthenes.

Lower molecular weight, linear olefins are readily hydrogenated by hydrogenation catalysts. However, higher molecular weight, highly branched olefins (oligomers) are more difficult to hydrogenate, particularly to high conversions (i.e., low bromine index—B.I.). In conjunction with a particular run, the comparative activity of the catalyst of the present invention in the hydrogenation of $C_{12}$ U.O.P. olefin, tetrapropylene, has been studied. A feed of 1 part tetrapropylene and 3 parts hydrogenated product was used to simulate the actual feed composition entering the reactor in an operation which employs product recycle to maintain temperature control.

During this study an attempt was also made to simulate the blocked operation in the plant with two different feedstocks. First, the tetrapropylene-containing feedstock with a bromine index of 25,000 was introduced into the catalyst bed and then maintained for several days. Next, the tetrapropylene feedstock was replaced by a mineral spirits feedstock containing 21.7% aromatics. After more than 3 days on mineral spirits, the tetrapropylene feedstock again become the feed to the unit for the next few days. All of these steps were at a constant temperature of 320° F. and the resulting bromine indices of the products were measured. At this point the temperatures of the respective catalyst beds were increased first to 450° F. and then to 470° F. to determine if specification quality product (<120 bromine index) was attainable at the high temperature. In addition to outperforming commercial Catalyst L all through the run, the catalyst of the present invention was able to achieve on specification quality at the higher bed temperatures. Commercial Catalyst L was unable to achieve a bromine index below 1500 at the highest temperature.

As previously indicated, the copper promoted massive nickel catalysts of the present invention are characterized as being capable of having a reduced nickel surface area ranging from about 55 to about 100 m²/g and a B.E.T. total surface area ranging from about 150 to about 300 m²/g and preferably ranging from about 225 m²/g to about 300 m²/g. The reduced nickel surface area of the catalyst is determined by hydrogen chemisorption wherein the catalyst has been reduced with hydrogen at 400° C. The procedure used to determine the hydrogen chemisorption is described by D. J. F. Yates, W. F. Taylor and J. H. Sinfelt, *J. Am. Chem. Soc.* 86, 2996–3001 (1964). As in the case of the coppernickel alloys described by J. H. Sinfelt, J. L. Carter and D. J. C. Yates, *J. of Catalysis*, 24, 283–296 (1972) and J. H. Sinfelt, *Science*, 195, 641–646 (1977) the copper tends to concentrate in the surface of the copper promoted massive nickel catalyst. This in effect reduces the surface area on which the hydrogen can be absorbed by the hydrogen chemisorption test. X-ray diffraction analysis by line broadening has revealed, however, that the crystallite sizes of the nickel in the copper promoted massive nickel catalyst is substantially the same as the massive nickel catalysts which have not been promoted by the copper. It has been found that in either case the nickel crystallites for both catalysts as determined by x-ray diffraction by line broadening ranges from about 10 to 50 Å preferably from 15 to 30 Å in size. Typically, these catalysts have nickel crystallites of 20-21 Å in size. The crystallites in the massive nickel catalysts are smaller than the crystallites in similar commercially available nickel catalysts. The smaller the crystallites the larger the number of surface atoms available for hydrogen chemisorption.

While reference in the specification is made to using water soluble salts of nickel and copper in the preparation of the catalyst of the present invention, it will be understood that these salts may be prepared in situ from other sources, such as by treating the metals with nitric acid to convert the nickel and copper metals to their nitrate salts.

The catalyst of the present invention can be put to use in a variety of hydrogenation reactions. As previously indicated the catalyst of the present invention has been found useful in converting aromatics to cycloaliphatic compounds (e.g., benzene to cyclohexane and aromatics to naphthenes, i.e., the conversion of white spirits); the conversion of olefins to saturated aliphatic compounds (e.g., the conversion of tetrapropylene to the corresponding saturated aliphatic compound) and the conversion of aldehydes to alcohols (e.g., benzaldehyde to benzyl alcohol, acetaldehyde to ethanol and other aromatic or aliphatic aldehydes to their corresponding alcohols). In addition, the catalyst of the present invention may be used to convert nitriles to amines (e.g., conversion of $C_{12}$ to $C_{24}$ nitriles to the corresponding fatty acid amines); aromatic nitro compounds to amines (e.g., nitrobenzene to aniline); aromatic amines to cycloaliphatic amines (e.g., aniline to cyclohexylamine); mistyl oxide to methyl isobutyl ketone; dextrose to sorbitol; and conversion of unsaturated edible fats and oils to partial and totally saturated fats and oils. The catalyst of the present invention can be used in decolorizing various organic compounds e.g., hydrocarbon feedstocks and oxygenated organic compounds as well as act as a sulfur scavenger for various hydrocarbon feedstocks. When the catalyst is put to the foregoing uses, the well known hydrogenation conditions for the specific reactions can be employed. Broadly, the foregoing hydrogenations may utilize temperatures ranging from 75°–300° C.; pressures ranging from 1 atm to 12,000 psig; space velocities ranging from a feed rate ranging from 0.2 to 100 V/Hr./V; and an $H_2$ rate ranging from 500 to 10,000 SCF/B.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A process for hydrogenating organic compounds which comprises contacting at least one hydrogenatable organic compound with hydrogen in the presence of a calcined and reduced coprecipitated copper-nickel-silica catalyst capable of having an active nickel surface area ranging from about 55 m²/g to about 100 m²/g as determined by hydrogen chemisorption, after reduction at 400° C. and a B.E.T. total surface area ranging from about 150 m²/g to about 300 m²/g, wherein said catalyst contains from about 2 wt. % to about 10 wt. % copper and about 25 wt. % to about 50 wt. % of nickel, said wt. % of copper and nickel being based on the total weight of the catalyst.

2. The process of claim 1 wherein the catalyst contains about 0.1 wt. % or less sodium based on the total weight of the active catalyst.

3. The process of claim 1 wherein said porous support comprises kieselguhr.

4. The process of claim 1 wherein said hydrogenation is conducted at a temperature ranging from about 75° C. to about 300° C., at a pressure ranging from about 1 atmosphere to about 12,000 psig, at a space velocity feed rate ranging from about 0.2 to about 100 V/Hr./V and at a H₂ rate ranging from about 500 to about 10,000 SCF/B.

5. The process of claim 1 wherein at least one of the organic compounds is benzene.

6. The process of claim 1 wherein at least one of the organic compounds is an aldehyde.

7. The process of claim 1 wherein the organic compounds include a mixture of a paraffin and at least one olefin.

8. The process of claim 1 wherein the organic compound is a mixture of a paraffin and an aromatic hydrocarbon.

9. The process of claim 1 wherein the catalyst has been activated with a reductant to an active state at temperatures ranging from about 80° C. to about 250° C.

10. The process of claim 1 wherein the catalyst has been prepared by the process comprising:
    (a) preparing an aqueous mixture containing nickel, copper and silicate ions and solid porous carrier particles under conditions of dilution such that the amount of dissolved nickel in said aqueous mixture is below 0.60 mole/liter;
    (b) heating the aqueous mixture; and
    (c) adding a precipitating agent to coprecipitate the dissolved copper, nickel and silicate ions with the solid porous carrier particles.

11. A process for hydrogenating organic compounds which comprises contacting at least one hydrogenatable organic compounds with hydrogen in the presence of a calcined and reduced coprecipitated copper-nickel-silica catalyst being characterized as having a reduced nickel surface area ranging from about 55 to about 100 m²/g as determined by hydrogen chemisorption, after reduction at 400° C. and a B.E.T. total surface area ranging from about 150 to about 300 m²/g, wherein the catalyst contains about 0.1 wt. % or less sodium based on the total weight of the active catalyst and the amount of copper in the catalyst ranges from about 2 wt. % to about 10 wt. % and the amount of nickel in the catalyst ranges from about 25 wt. % to about 50 wt. %, said wt. % of copper and nickel based on the total weight of the catalyst, said catalyst having been prepared by the process comprising:
    (a) uniformly comingling a first aqueous solution containing silicate anions and solid porous carrier particles comprising kieselguhr with a second solution containing nickel and copper cations under conditions of dilution such that the amount of dissolved nickel in the comingled reaction solution is below 0.60 moles/liter;
    (b) heating the comingled reaction mixture;
    (c) adding a precipitating agent to coprecipitate the copper, nickel and silicate with said solid porous carrier kieselguhr particles;
    (d) drying said coprecipitated catalyst and calcining it at a temperature ranging from 300° to 450° C.; and
    (e) reducing the calcined catalyst with a gaseous reductant at temperatures ranging from about 75° C. to about 400° C. until said catalyst has been activated by the reduction.

12. The process in accordance with claim 11 wherein the concentration of the kieselguhr ranges from about 10 wt. % to about 70 wt. % of the total silica in the catalyst.

13. The process in accordance with claim 11 wherein the concentration of the kieselguhr ranges from about 30 wt. % to about 50 wt. % based on the total silica in the catalyst.

14. The process in accordance with claim 11 wherein the calcined catalyst has been reduced with a reductant to an active state at temperatures ranging from about 80° C. to about 250° C.

15. The process in accordance with claim 11 wherein said hydrogenation is conducted at a temperature ranging from about 75° C. to about 300° C., at a pressure ranging from about 1 atmosphere to about 12,000 psig, at a space velocity feed rate ranging from about 0.2 to about 100 V/Hr./V and at a H₂ rate ranging from about 500 to about 10,000 SCF/B.

* * * * *